United States Patent
Rzany et al.

(10) Patent No.: US 8,507,101 B2
(45) Date of Patent: *Aug. 13, 2013

(54) BIOCORRODIBLE IMPLANT HAVING A CORROSION-INHIBITING COATING

(75) Inventors: Alexander Rzany, Nuremberg (DE); Heinz Mueller, Erlangen (DE)

(73) Assignee: Biotronik VI Patent AG, Baar (CH)

( * ) Notice: Subject to any disclaimer, the term of this patent is extended or adjusted under 35 U.S.C. 154(b) by 205 days.

This patent is subject to a terminal disclaimer.

(21) Appl. No.: 12/915,331

(22) Filed: Oct. 29, 2010

(65) Prior Publication Data

US 2011/0144761 A1    Jun. 16, 2011

Related U.S. Application Data

(60) Provisional application No. 61/285,190, filed on Dec. 10, 2009.

(51) Int. Cl.
*A61F 2/28*  (2006.01)
*B05D 3/02*  (2006.01)

(52) U.S. Cl.
USPC .......... 428/469; 148/239; 623/23.6; 623/1.46

(58) Field of Classification Search
None
See application file for complete search history.

(56) References Cited

U.S. PATENT DOCUMENTS

| | | | | | |
|---|---|---|---|---|---|
| 5,161,728 A | * | 11/1992 | Li | ............................... | 228/124.1 |
| 5,725,573 A | * | 3/1998 | Dearnaley et al. | ........... | 427/2.25 |
| 5,939,208 A | * | 8/1999 | Stoy | ............................... | 428/500 |
| 6,207,218 B1 | * | 3/2001 | Layrolle et al. | ............... | 427/2.27 |
| 6,916,772 B2 | * | 7/2005 | Zhou et al. | ..................... | 510/201 |
| 8,057,536 B2 | * | 11/2011 | Mueller et al. | ............... | 623/1.46 |
| 2005/0191408 A1 | * | 9/2005 | Aharonov et al. | ........... | 427/2.27 |
| 2008/0015578 A1 | * | 1/2008 | Erickson et al. | ................ | 606/61 |
| 2008/0103594 A1 | * | 5/2008 | Loffler et al. | ............... | 623/11.11 |
| 2008/0183278 A1 | * | 7/2008 | Atanasoska et al. | ......... | 623/1.17 |
| 2008/0243242 A1 | * | 10/2008 | Kappelt et al. | ................ | 623/1.46 |
| 2008/0262589 A1 | * | 10/2008 | Nagura | .......................... | 623/1.2 |
| 2008/0312736 A1 | * | 12/2008 | Mueller et al. | ............... | 623/1.46 |
| 2009/0069884 A1 | * | 3/2009 | Mueller | ....................... | 623/1.46 |
| 2009/0093881 A1 | * | 4/2009 | Bandyopadhyay et al. | .......................... | 623/16.11 |
| 2010/0280601 A1 | * | 11/2010 | Hofer et al. | .................. | 623/1.46 |
| 2011/0319986 A1 | * | 12/2011 | Bayer et al. | .................. | 623/1.46 |

* cited by examiner

Primary Examiner — Vera Katz
(74) Attorney, Agent, or Firm — Greer, Burns & Crain Ltd.

(57) ABSTRACT

A biocorrodible implant includes a base formed from magnesium or a biocorrodible magnesium alloy, whose surface has a corrosion-inhibiting coating. A diffusion layer, which covers the base, differs in composition from the implant material. The diffusion layer contains at least one metallic element of the implant material and at least one corrosion-inhibiting element selected from the group of Al, Zn, Ca, Si, In, Mn, Sc and RE, where RE stands for rare earth metals. The implant optionally includes a metal layer of at least one of the corrosion-inhibiting elements selected from the group of Al, Zn, Ca, Si, In, Mn, Sc and RE covering the diffusion layer, and a passivating layer of metal oxides, metal nitrides or metal fluorides of at least one of the corrosion-inhibiting elements selected from the group of Al, Zn, Ca, Si, In, Mn, Sc and RE covering the diffusion layer or the metal layer.

10 Claims, 4 Drawing Sheets

US 8,507,101 B2

BIOCORRODIBLE IMPLANT HAVING A CORROSION-INHIBITING COATING

CROSS REFERENCE

The present application claims priority on co-pending U.S. provisional application No. 61/285,190 filed on Dec. 10, 2009; which application is incorporated by reference herein.

FIELD

One aspect of the invention relates to a biocorrodible implant based on magnesium or a biocorrodible magnesium alloy, whose surface has a corrosion-inhibiting coating. Furthermore, another aspect of the invention relates to a respective manufacturing method for the coating.

BACKGROUND

An implant is understood in general to be any mechanical device (whether including moving parts or not) made of one or more materials which is intentionally introduced into the body and is covered either partially or completely by an epithelial surface. Implants can be subdivided into temporary and permanent implants with regard to the duration of use. Temporary implants remain in the body for a certain period of time. Permanent implants are intended to remain in the body permanently. Implants can also be differentiated according to prostheses and artificial organs. A prosthesis is a medical device which replaces extremities, organs or tissues of the body, whereas an artificial organ is understood to be a medical device that partially or completely replaces the function of an organ of the body. Implants such as orthopedic or osteosynthetic implants, cardiac pacemakers, defibrillators and vascular implants, for example, fall under the definitions given above.

An implant material is a nonviable material, which is used for an application in medicine and enters into interactions with biological systems. Biocompatibility is the basic prerequisite for use of a material as an implant material coming in contact with the biological environment when used as intended. Biocompatibility is understood to be the ability of a material to induce an appropriate tissue reaction in a specific application. This includes an adaptation of the chemical, physical, biological and morphological surface properties of an implant to the recipient tissue with the goal of a clinically desired interaction. The biocompatibility of the implant material also depends on the chronological course of the reaction of the biosystem in which it is implanted. Thus relatively short-term irritation and inflammation occur, possibly leading to tissue changes in the medium to long range, toxicity, allergies or even cancer by the results of inadequate biocompatibility.

The response of biological systems to foreign bodies depends on the properties of the material or component in a variety of ways. According to the response of the biosystem, the implant materials may be subdivided into bioactive, bioinert and degradable/resorbable materials.

For the purposes of the present invention, metallic implant materials consisting entirely or in part of magnesium or biocorrodible magnesium alloys are of interest, their application being in osteosynthesis, joint replacement, dental surgery and vascular surgery, for example.

One problem with the use of biocorrodible magnesium alloys is the rapid degradation of the material in a physiological environment. The principles of magnesium corrosion as well as some technical methods for improving corrosion properties (in the sense of strengthening the protection against corrosion) are known from the prior art. Such known methods, however, have unresolved problems and disadvantages associated with them.

Methods of creating a corrosion-preventing layer have not been developed for medical technical use of biocorrodible implants in a physiological environment.

Traditional technical fields of use of molded bodies of magnesium alloys outside of medical technology usually require extensive suppression of corrosive processes. Accordingly, the goal of most known technical methods is to completely eliminate corrosive processes. However, such methods may not be desirable for medical implant applications. Furthermore, for a medical technical use, toxicological aspects must also be taken into account. Furthermore, corrosive processes depend greatly on the medium in which they take place, and therefore findings obtained about corrosion prevention in the technical field under traditional ambient conditions should not be applicable to an unlimited extent to the processes in a physiological environment. Finally, with a variety of medical implants, the mechanisms underlying the corrosion could also deviate from conventional technical applications of the material. For example, stents, surgical material or clips undergo mechanical deformation during use, so the partial process of stress corrosion cracking should play a major role in the degradation of these molded bodies.

The basic body of some implants such as stents in particular is subject to plastic deformation of different intensities locally during use. Conventional methods for inhibiting corrosion, e.g., generation of a dense magnesium oxide cover layer, are not helpful here. The ceramic properties of such a cover layer would result in the cover layer flaking off locally. Corrosion would then take place uncontrollably, and there would be the risk in particular that corrosion might be induced in the areas of the implant subject to especially great mechanical stress.

SUMMARY

One object of some embodiments of the present invention is to eliminate or at least reduce one or more of the problems described here. In particular, coatings of some implant embodiments have a high adhesive power and nevertheless ensure adequate deformability.

A first aspect of one invention embodiment lies in providing an implant, comprising
(i) an implant material comprising magnesium or a biocorrodible magnesium alloy forming a base; and
(ii) a diffusion layer which covers the base and differs in its composition from the implant material and contains at least one of the metallic elements of the implant material and at least one corrosion-inhibiting element selected from the group of Al, Zn, Ca, Si, In, Mn, Sc and RE, where RE stands for rare earth metals.

A second aspect of an invention embodiment includes the optional element:
(iii) optionally a metal layer of at least one of the corrosion-inhibiting elements selected from the group of Al, Zn, Ca, Si, In, Mn, Sc and RE, covering the diffusion layer.

A third aspect of an invention embodiment includes the optional element:
(iv) optionally a passivating layer of metal oxides, metal nitrides or metal fluorides of at least one of the corrosion-inhibiting elements selected from the group of Al, Zn, Ca, Si, In, Mn, Sc and RE, covering the diffusion layer or the metal layer.

Another aspect of an invention embodiment lies in providing a method for surface modification of an implant, or a method for manufacturing the aforementioned diffusion layer. One example inventive method comprises the steps:
(i) providing an untreated implant with an implant material of magnesium or a biocorrodible magnesium alloy forming the base;
(ii) contacting the surface of the base with a corrosion-inhibiting element selected from the group of Al, Zn, Ca, Si, In, Mn, Sc and RE, where RE stands for rare earth metals; and
(iii) simultaneously with or following step (ii), thermal treatment of the implant at least in the area of the contact surface, forming a diffusion layer which covers the base and contains at least one of the metallic elements of the implant material and at least one corrosion-inhibiting element selected from the group of Al, Zn, Ca, Si, In, Mn, Sc and RE.

DETAILED DESCRIPTION

Figure 1:
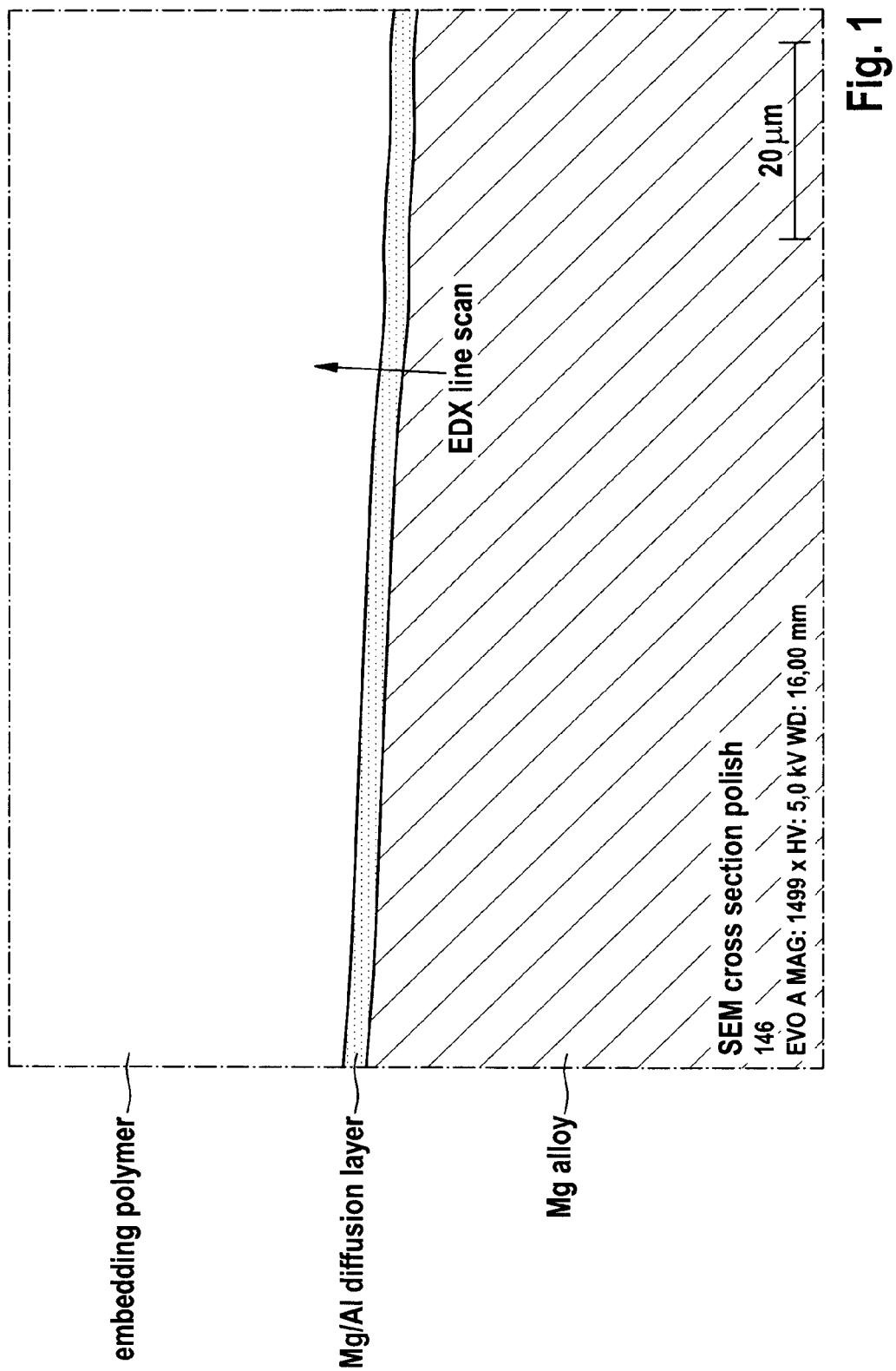
FIG. 1 shows a section through the sample body having an inventive diffusion layer.

A first aspect of an invention embodiment lies in providing an implant, comprising
(i) an implant material comprising magnesium or a biocorrodible magnesium alloy forming a base;
(ii) a diffusion layer which covers the base and differs in its composition from the implant material and contains at least one of the metallic elements of the implant material and at least one corrosion-inhibiting element selected from the group of Al, Zn, Ca, Si, In, Mn, Sc and RE, where RE stands for rare earth metals;
(iii) optionally a metal layer of at least one of the corrosion-inhibiting elements selected from the group of Al, Zn, Ca, Si, In, Mn, Sc and RE, covering the diffusion layer;
(iv) optionally a passivating layer of metal oxides, metal nitrides or metal fluorides of at least one of the corrosion-inhibiting elements selected from the group of Al, Zn, Ca, Si, In, Mn, Sc and RE, covering the diffusion layer or the metal layer.

It is noted that the "optional" elements identified above are indeed optional only. Some invention embodiments include them, while others do not. The base may be comprised of any of a number of suitable materials in suitable concentrations. One example base comprises at least about 5.8% (wt) rare earth metals and at least about 93.7% (wt) magnesium or magnesium alloy. Another example base comprises at least about 3.9% Y, at least about 2.9% additional rare earth metals. Some example bases further comprise Zr.

One example inventive diffusion layer, as will be explained in greater detail below, is formed by thermal treatment of a basic implant body of magnesium and/or a biocorrodible magnesium alloy covering the corrosion-inhibiting element. The diffusion layer differs in composition from the implant material, but because of the manufacturing process it contains at least one of the metallic elements of the implant material. This is usually at least magnesium. Furthermore, the diffusion layer contains one or more elements Al, Zn, Ca, Si, In, Mn, Sc and RE. The metallic diffusion layer may also contain other elements. An example metallic diffusion layer has a ductility comparable to that of the base material at least close to the base of the implant, so that deformation of the implant, such as that occurring as part of dilatation of a stent, for example, may take place without developing cracks or flaking of the corrosion-inhibiting coating. The layer thickness of an example diffusion layer is predefined so that when cracks occur or when so-called sliding stages unavoidably escape during plastic deformation, this damage to the original surface does not extend down into the base material but instead extends only into an area where the corrosion-inhibiting element is still accumulated, thus avoiding local corrosion.

The collective term "rare earth metals" is understood in the present case to include any one or more of yttrium (39), lanthanum (57) and the 14 elements following lanthanum (57), namely cerium (58), praseodymium (59), neodymium (60), promethium (61), samarium (62), europium (63), gadolinium (64), terbium (65), dysprosium (66), holmium (67), erbium (68), thulium (69), ytterbium (70) and lutetium (71). The concentration of the RE in diffusion layer embodiments of the invention will vary with application.

"Biocorrodible" in the sense of the invention is understood to refer to magnesium alloys in which degradation/restructuring take place in a physiological environment, so that the part of the implant made of this material is completely or at least predominantly no longer present after a sufficient period of time. The magnesium alloy in the present case is understood to be a metallic structure whose main component is magnesium. The main component is the alloy component whose proportion by weight in the alloy is the greatest. The proportion of the main component is in some embodiments is more than 50 wt %, and in some other embodiments is more than 70 wt %. Many other compositions are also possible in other invention embodiments, with examples including less than 50 wt % and greater than 70%.

The composition of the magnesium alloy in many embodiments is selected so that it is biocorrodible. Synthetic plasma such as that specified according to EN ISO 10993-15:2000 for biocorrosion tests (composition in NaCl 6.8 g/L, $CaCl_2$ 0.2 g/L, KCl 0.4 g/L, $MgSO_4$ 0.1 g/L, $NaHCO_3$ 2.2 g/L, $Na_2HPO_4$ 0.126 g/L, $NaH_2PO_4$ 0.026 g/L) is used as the test medium for testing the corrosion behavior of an alloy in question. A sample of the alloy to be tested is stored in a sealed sample container with a defined quantity of the test medium at 37° C. At intervals of time—coordinated with the corrosion behavior to be expected—of a few hours up to several months, the samples are removed and tested for traces of corrosion by known methods. The artificial plasma according to EN ISO 10993-15:2000 corresponds to a blood-like medium and thus constitutes a possibility of simulating a physiological environment reproducibly in the sense of the invention.

One example inventive diffusion layer may additionally be covered with a metal layer, which contains at least one of the aforementioned corrosion-inhibiting elements.

The concentration of the corrosion-inhibiting element in some diffusion layer embodiments drops from the outside of the implant toward the base. That is, the concentration is at a maximum at an outermost surface and decreases across the thickness of the layer to a minimum at a distal surface that is proximate to the implant. The concentration variance may be linear or adopt a different variance across the thickness of the layer. In this way, the properties of the material can be adjusted continuously to ensure a very high adhesion power. Such a configuration provides other advantages as well, with an example being a variable rate of decay depending on the corrosion-inhibiting element at the current outer surface.

It is also within the scope of the present invention to design an example diffusion layer so that one or more corrosion-inhibiting elements follow a predefined corrosion profile over the thickness of the diffusion layer. This may take place, for example, by repeating steps (ii) and (iii) with different corrosion-inhibiting elements and/or under different conditions (in particular temperature and duration of the treatment). The predefined corrosion profile can be selected depending on application. In some embodiments, it can be selected to achieve a decreasing corrosion-inhibiting element concentration from the outside of the implant moving across the layer thickness inwardly toward the base.

According to a first example variant, the corrosion-inhibiting element is selected from the group of Zn, Ca, In, Mn, Sc and RE; the aforementioned elements are biocorrodible. Some example diffusion layers have a layer thickness of 0.05 µm to 20 µm. Many other thicknesses are possible, including smaller than 0.05 µm and greater than 20 µm. In addition or independently thereof, some examples of the optional metal layer have a layer thickness of 0.05 µm to 20 µm. Again, other thicknesses are within the scope of the invention. By using the aforementioned biocorrodible elements, thus relatively great layer thicknesses can be achieved for the diffusion layer and/or metal layer, which may be advantageous in selected areas of application.

According to an alternative second variant, the corrosion-inhibiting element is one or more of Al and Si, in particular Al. Al and Si are non-biocorrodible and accordingly the layer thickness of the diffusion layer is designed to be so small that gradual degradation of the implant is nevertheless possible. An example diffusion layer including Al and/or Si has a layer thickness in the range of 0.01 µm to 5 µm, with other thicknesses within the scope of the invention. The metal layer of Al and/or Si which is optionally still present may have a layer thickness in the range of 0.01 µm to 2 µm, with other thicknesses also useful in some applications.

Example embodiments of the inventive diffusion layer and/or the optional metal layer may also have other elements in addition to the corrosion-inhibiting elements, in particular elements having a pharmacological effect. These elements may comprise As, Se, Co, Cu and Ag or others that have a pharmacological effect.

Example embodiments of the inventive diffusion layer and/or the optional metal layer may also be covered by a passivating layer of metal oxides, metal nitrides or metal fluorides of at least one of the corrosion-inhibiting elements selected from the group of Al, Zn, Ca, Si, In, Mn, Sc and RE.

Example embodiments of the invention may be used with all implants comprising magnesium or biocorrodible magnesium alloys or having at least components of this implant material, which are in contact with the surrounding tissue after implantation.

Example implants of the invention are especially well suited to practice in the form of a vascular, orthopedic or osteosynthetic implant. One particularly useful embodiment of an implant is a stent. Still other implants are within the scope of the invention.

Another aspect of the invention lies in providing a method for surface modification of an implant, and a method for manufacturing the aforementioned diffusion layer. One example inventive method comprises the steps:

(i) providing an untreated implant with an implant material of magnesium or a biocorrodible magnesium alloy forming the base;
(ii) contacting the surface of the base with a corrosion-inhibiting element selected from the group of Al, Zn, Ca, Si, In, Mn, Sc and RE, where RE stands for rare earth metals; and
(iii) simultaneously with or following step (ii), thermal treatment of the implant at least in the area of the contact surface, forming a diffusion layer which covers the base and contains at least one of the metallic elements of the implant material and at least one corrosion-inhibiting element selected from the group of Al, Zn, Ca, Si, In, Mn, Sc and RE.

According to an example embodiment of an inventive method, the surface of the implant consisting of magnesium or the biocorrodible magnesium alloy is thus brought in contact with the corrosion-inhibiting elements, i.e., usually being coated with these elements. This may be accomplished by coating methods, e.g., vapor deposition, electrode beam coating or sputtering, for example. Other coating and deposition methods may also be practiced as will be appreciated by those knowledgeable in the art. In many embodiments, the metallic material is applied as homogeneously as possible to the base.

Simultaneously with the coating or in a subsequent separate method step, the temperature is adjusted so that a diffusion layer can develop. The temperature is to be preselected so that the mechanical integrity of the basic body is not significantly impaired. The temperature is thus at least below the melting point of magnesium and/or the biocorrodible magnesium alloy used. The use of corrosion-inhibiting elements such as Al, Zn, Ca, Si, In and rare earth metals, which form eutectic systems with magnesium, can be useful for this method. With non-eutectic systems, e.g., the use of Mn or Sc in particular, the diffusion layer is formed by thermally induced interdiffusion processes.

Step (iii) is performed in some embodiments so that the concentration of the corrosion-inhibiting element in the resulting diffusion layer declines from the outside of the implant to the base. That is, it is at a maximum near an outer surface and decreases across the layer thickness to a minimum proximate to the base.

The first thermal treatment may optionally be followed by a second thermal treatment in an oxygen-rich atmosphere. When using aluminum, for example, intensification of the passivation may be achieved by forming an oxide on the surface.

Furthermore, following step (ii) and simultaneously with step (iii) or following step (iii), a chemical reaction of the surface of the diffusion layer and/or metal layer with O, N or F may be performed, forming a nonmetallic passivating layer covering the implant. The chemical surface treatment leads to the development of a passivating layer of metal oxides, metal nitrides or metal fluorides of at least one of the corrosion-inhibiting elements, selected from the group of Al, Zn, Ca, Si, In, Mn, Sc and RE, covering the diffusion layer or metal layer. An additional passivating effect can be achieved in this way.

Example Embodiment

A basic body of a biocorrodible magnesium alloy for a stent is provided. The magnesium alloy has the following composition:

3.9 wt % Y;
2.9 wt % additional rare earth metals, not including Y;
0.4 wt % Zr; and
remainder (93.8%) magnesium and impurities due to the production process, less than 0.1 wt %.

The basic body is covered with a layer of aluminum approximately 2 µm to 4 µm thick by thermal vacuum deposition. Then the coated basic body is heated to 450° C. in air for 30 minutes, whereupon a diffusion layer forms, containing aluminum and magnesium.

Figure 2:
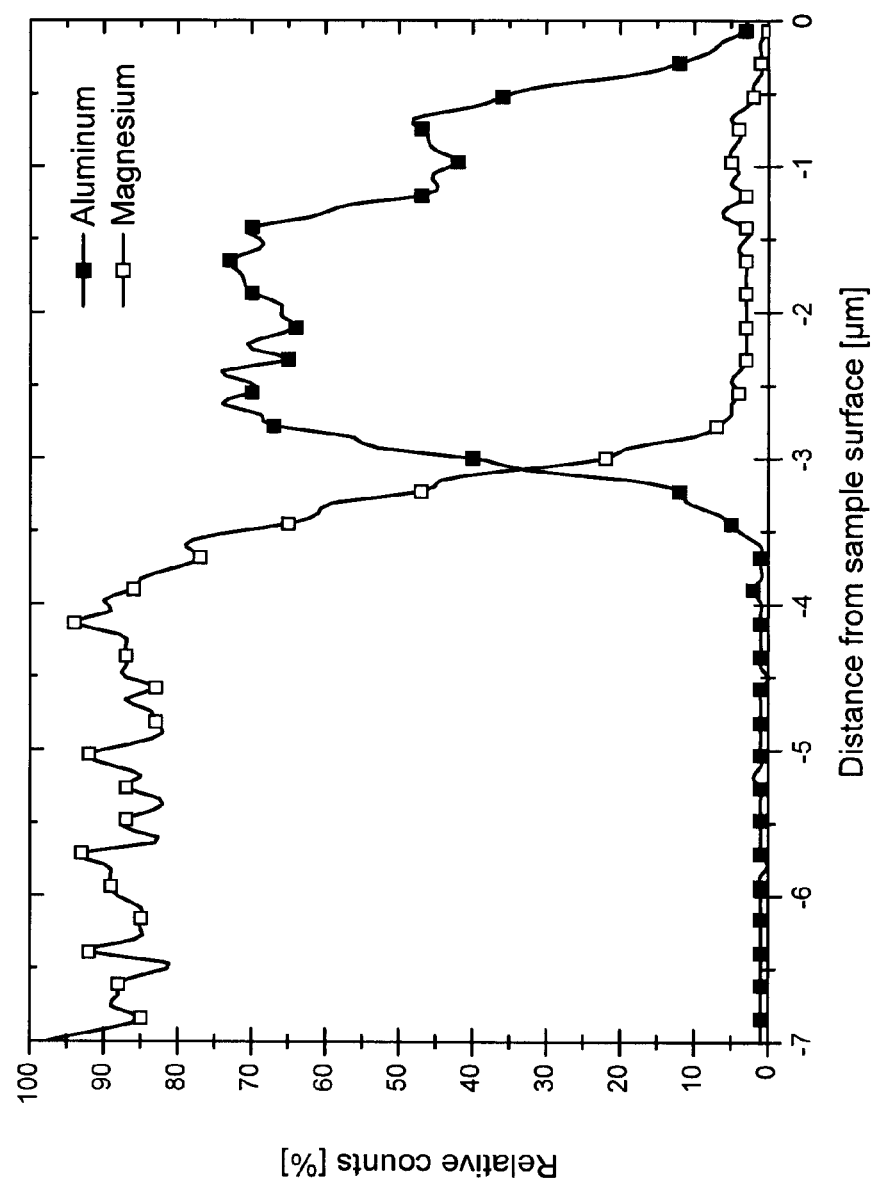
FIG. 2 shows an EDX scan of the sample body.
Figure 3:
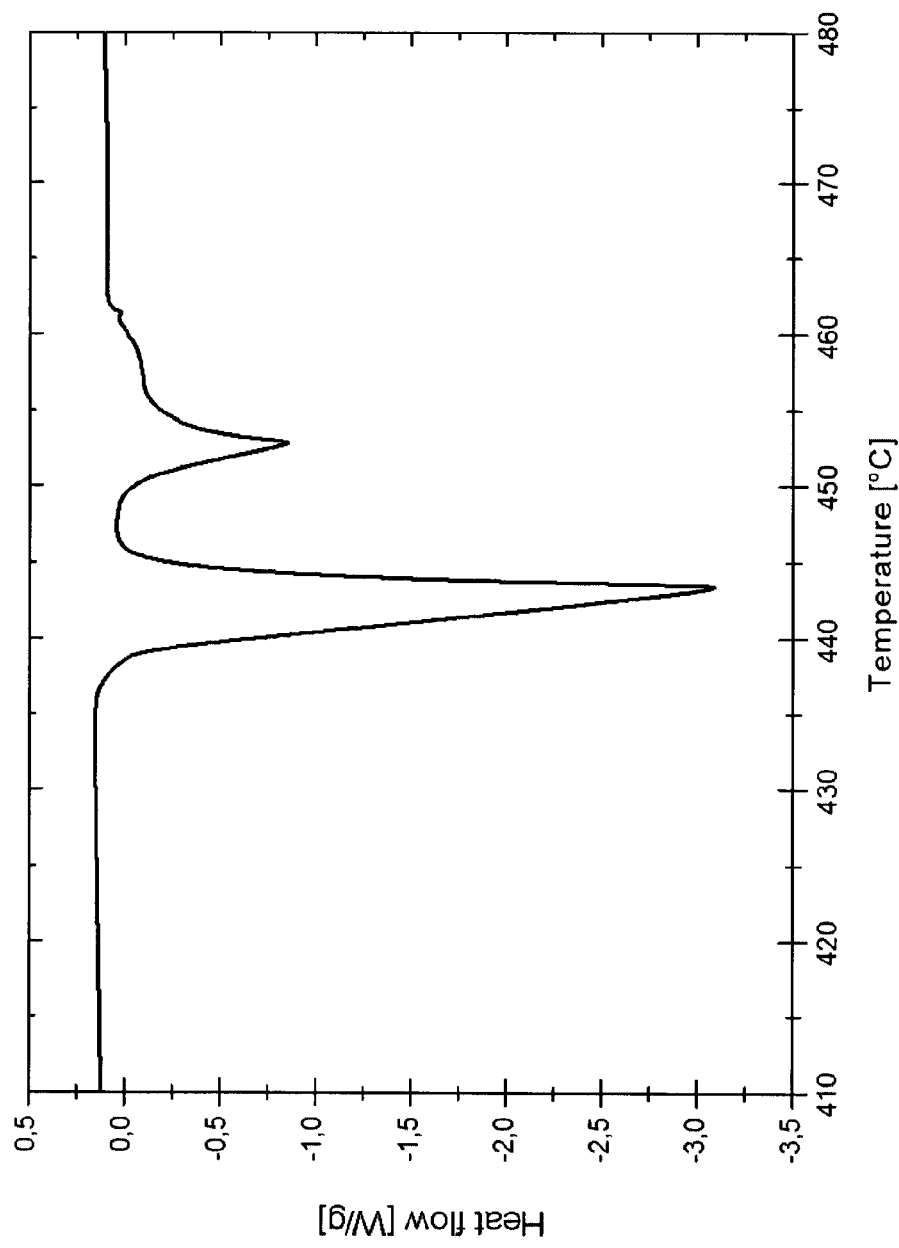
FIG. 3 shows a DSC curve of the same sample body.

FIG. 1 shows a section through the sample body of the interfaces between the base of the biocorrodible magnesium alloy and the diffusion layer formed due to the thermal treatment. An elemental analysis by the EDX method proves that an Al/Mg alloy has formed at the interface, its aluminum content increasing toward the outside (see FIG. 2). An accompanying DSC analysis (see FIG. 3) proves that two eutectics are formed at 437° C. and 450° C.

Figure 4:
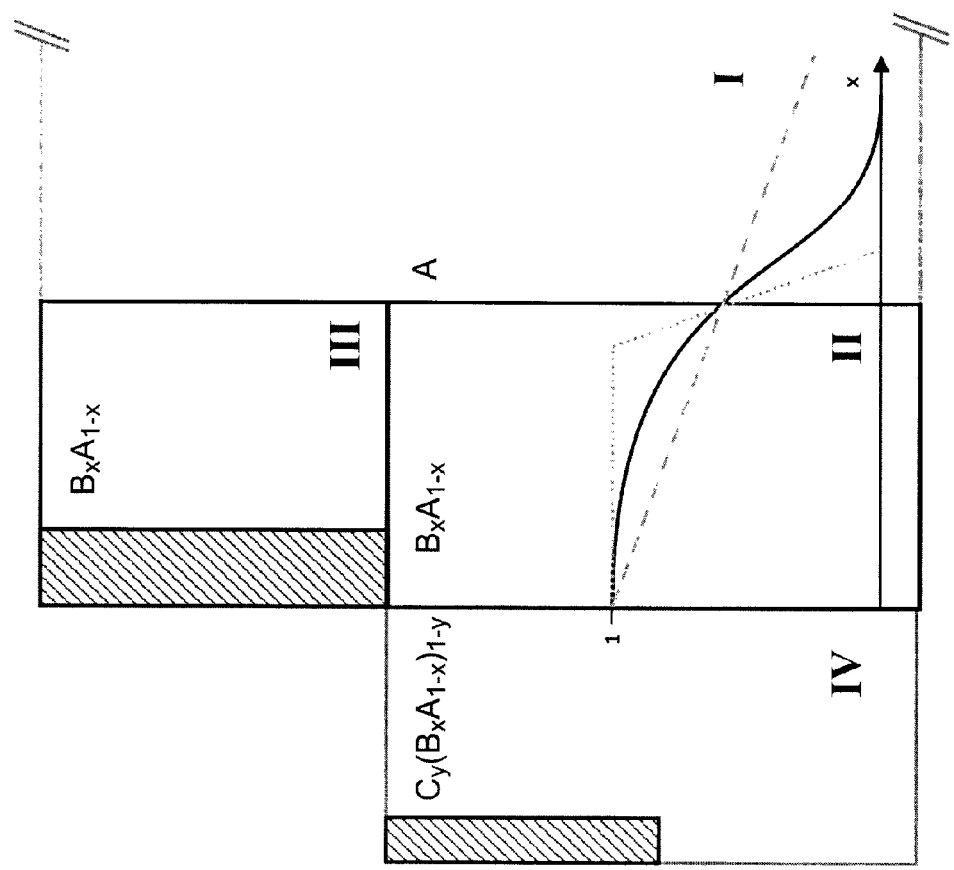
FIG. 4 shows a schematic diagram of possible layer sequences: (a) I+III: basic body of alloy A with diffusion layer B(x)A(1-x) and optional passivation of the surface; (b) I+II+IV: basic body of alloy A with diffusion layer B(x)A(1-x) and additional diffusion layer C(y)(B(x)A(1-x))(1-y) with optional passivation of the surface with a nonmetallic cover layer.

FIG. 4 illustrates schematically possible layer sequences (a) I+III: basic body of alloy A with diffusion layer B(x)A(1-x) and optional passivation of the surface (hatched area); (b) I+II+IV: basic body of alloy A with diffusion layer B(x)A(1-x) and additional diffusion layers C(y)(B(x)A(1-x))(1-y) with optional passivation of the surface with a nonmetallic top layer (hatched area).

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention. Description of a method of the invention will be understood to include description of apparatuses of the invention, and vice versa.

What is claimed is:

1. A biocorrodible implant, comprising
   (i) an implant material comprising magnesium or a biocorrodible magnesium alloy and at least one rare earth metal forming a base; and,
   (ii) a diffusion layer having a thickness of between about 0.01 μm to 20 μm which covers the base and differs in its composition from the base and contains at least one metallic element of the base and at least one corrosion-inhibiting element selected from the group of Al, Zn, Ca, Si, In, Mn, Sc and RE, the concentration of the corrosion-inhibiting element decreasing across the thickness of the diffusion layer from a maximum at an uppermost surface to a lowest concentration at a distal surface proximate the base;
   (iii) a metal layer having a thickness of between about of 0.01 μm to 20 μm and comprised of at least one of the corrosion-inhibiting elements selected from the group of Al, Zn, Ca, Si, In, Mn, Sc and RE, covering the diffusion layer; and
   (iv) a passivating layer of metal oxides, metal nitrides or metal fluorides of at least one of the corrosion-inhibiting elements selected from the group of Al, Zn, Ca, Si, In, Mn, Sc and RE, covering the diffusion layer or metal layer.

2. The implant according to claim 1, wherein the corrosion-inhibiting element is selected from the group of Zn, Ca, In, Mn, Sc and RE.

3. The implant according to claim 1, wherein the diffusion layer has a layer thickness in the range of 0.05 μm to 20 μm.

4. The implant according to claim 1, wherein the corrosion-inhibiting element is Al and/or Si.

5. The implant according to claim 4, wherein the diffusion layer has a layer thickness in the range of 0.01 μm to 5 μm.

6. The implant according to claim 1, wherein the implant is an orthopedic or osteosynthetic implant.

7. The implant according to claim 1, wherein the implant is a vascular implant.

8. The implant according to claim 1, wherein the base comprises at least about 5.8% (wt.) rare earth metals including at least Y, and at least about 93.7% (wt.) magnesium.

9. The implant according to claim 1, wherein the metal layer has a layer thickness in the range of 0.01 μm to 2 μm.

10. The implant according to claim 1, wherein the metal layer has a layer thickness in the range of 0.05 μm to 20 μm.

* * * * *